(12) United States Patent
Espinoza

(10) Patent No.: US 6,558,398 B1
(45) Date of Patent: May 6, 2003

(54) DEPLITORY DEVICE

(76) Inventor: Gloria C. Espinoza, 582 Oaklawn Ave., Chula Vista, CA (US) 91910

( * ) Notice: Subject to any disclaimer, the term of this patent is extended or adjusted under 35 U.S.C. 154(b) by 0 days.

(21) Appl. No.: 09/928,096

(22) Filed: Aug. 10, 2001

(51) Int. Cl.[7] .................. A61B 17/50; A61M 1/00
(52) U.S. Cl. .................. 606/133; 606/211; 604/35
(58) Field of Search .................. 606/131, 133, 606/134, 211, 205–210; 294/99.1, 99.2, 100; 604/117, 234–35

(56) References Cited

U.S. PATENT DOCUMENTS

| | | | |
|---|---|---|---|
| 849,789 A | | 4/1907 | Hurd |
| 1,276,495 A | * | 8/1918 | Crockett .................. 604/316 |
| 1,294,384 A | * | 2/1919 | Logeman .................. 242/137.1 |
| D138,784 S | | 12/1944 | Shonta |
| 2,803,252 A | | 8/1957 | Bloome |
| 3,576,072 A | * | 4/1971 | Foster .................. 30/124 |
| 4,040,184 A | * | 8/1977 | Hightower .................. 30/298 |
| 4,498,474 A | | 2/1985 | Chalmers et al. |
| 4,865,034 A | | 9/1989 | Van Der Molen |
| 5,133,722 A | | 7/1992 | Avrahami et al. |
| 5,536,251 A | * | 7/1996 | Evard et al. .................. 128/DIG. 26 |
| 5,971,081 A | | 10/1999 | Stewart |
| 6,159,222 A | * | 12/2000 | Yiu .................. 606/131 |
| 6,298,922 B1 | * | 10/2001 | Stewart .................. 169/46 |

* cited by examiner

Primary Examiner—Michael J. Milano
Assistant Examiner—Gwen Phanijphand

(57) ABSTRACT

A deplitory device for the removal of unwanted hair. The deplitory device includes a heatable tweezer having an upper portion containing wax that is dispensable onto a user's hair, allowing the user to utilize the tweezer to remove the cured wax thereby removing the hair from its follicle.

3 Claims, 1 Drawing Sheet

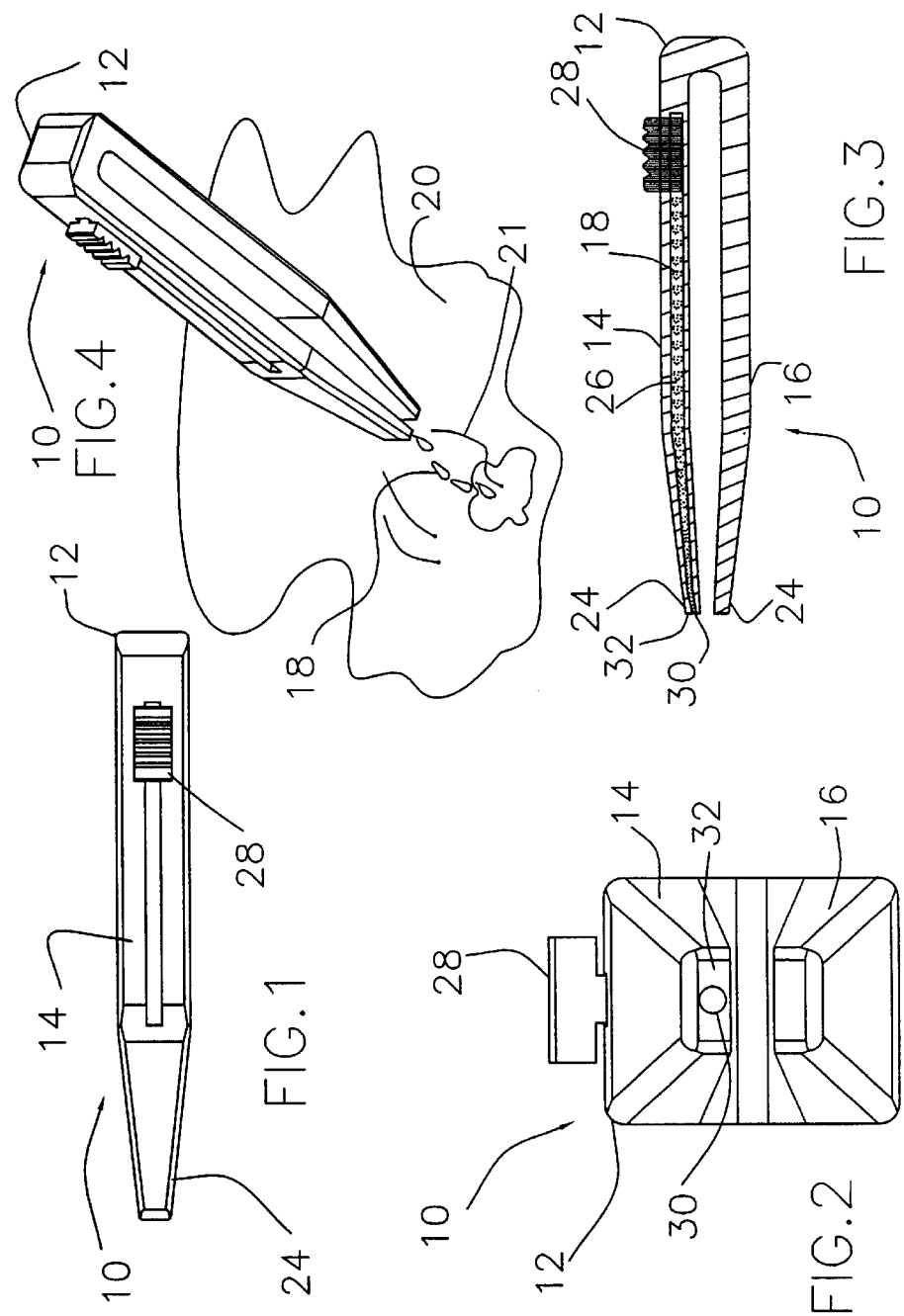

DEPLITORY DEVICE

BACKGROUND OF THE INVENTION

1. Field of the Invention

The present invention relates to tweezers and more particularly pertains to a new deplitory device for the removal of unwanted hair.

2. Description of the Prior Art

The use of tweezers is known in the prior art. More specifically, tweezers heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,133,722; U.S. Pat. No. 4,498,474; U.S. Pat. No. 5,971,081; U.S. Pat. No. 4,865,034; U.S. Pat. No. 2,803,252; U.S. Pat. No. 849,789; and U.S. Pat. No. Des. 138,784.

While these devices fulfill their respective, particular objectives and requirements, the aforementioned patents do not disclose a new deplitory device. The inventive device includes a heatable tweezer having an upper portion containing wax that is dispensable onto a user's hair, allowing the user to utilize the tweezer to remove the cured wax thereby removing the hair from its follicle.

In these respects, the deplitory device according to the present invention substantially departs from the conventional concepts and designs of the prior art, and in so doing provides an apparatus primarily developed for the purpose of the removal of unwanted hair.

SUMMARY OF THE INVENTION

In view of the foregoing disadvantages inherent in the known types of tweezers now present in the prior art, the present invention provides a new deplitory device construction wherein the same can be utilized for the removal of unwanted hair.

The general purpose of the present invention, which will be described subsequently in greater detail, is to provide a new deplitory device apparatus and method which has many of the advantages of the tweezers mentioned heretofore and many novel features that result in a new deplitory device which is not anticipated, rendered obvious, suggested, or even implied by any of the prior art tweezers, either alone or in any combination thereof.

To attain this, the present invention generally comprises a heatable tweezer having an upper portion containing wax that is dispensable onto a user's hair, allowing the user to utilize the tweezer to remove the cured wax thereby removing the hair from its follicle.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new deplitory device apparatus and method which has many of the advantages of the tweezers mentioned heretofore and many novel features that result in a new deplitory device which is not anticipated, rendered obvious, suggested, or even implied by any of the prior art tweezers, either alone or in any combination thereof.

It is another object of the present invention to provide a new deplitory device which may be easily and efficiently manufactured and marketed.

It is a further object of the present invention to provide a new deplitory device which is of a durable and reliable construction.

An even further object of the present invention is to provide a new deplitory device which is susceptible of a low cost of manufacture with regard to both materials and labor, and which accordingly is then susceptible of low prices of sale to the consuming public, thereby making such deplitory device economically available to the buying public.

Still yet another object of the present invention is to provide a new deplitory device which provides in the apparatuses and methods of the prior art some of the advantages thereof, while simultaneously overcoming some of the disadvantages normally associated therewith.

Still another object of the present invention is to provide a new deplitory device for the removal of unwanted hair.

Yet another object of the present invention is to provide a new deplitory device which includes a heatable tweezer having an upper portion containing wax that is dispensable onto a user's hair, allowing the user to utilize the tweezer to remove the cured wax thereby removing the hair from its follicle.

Still yet another object of the present invention is to provide a new deplitory device that utilizes self-contained wax to remove hair.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic top view of a new deplitory device according to the present invention.

FIG. 2 is a schematic end view of the present invention.

FIG. 3 is a schematic cross-sectional view of the present invention.

FIG. 4 is a schematic perspective view of the present invention in use.

DESCRIPTION OF THE PREFERRED EMBODIMENT

With reference now to the drawings, and in particular to FIGS. 1 through 4 thereof, a new deplitory device embodying the principles and concepts of the present invention and generally designated by the reference numeral 10 will be described.

As best illustrated in FIGS. 1 through 4, the deplitory device 10 generally comprises a tweezer 12. The tweezer 12 comprises an upper portion 14 and a lower portion 16. The tweezer 12 is heatable such that wax 18 contained in the upper portion 14 is dispensable onto the skin 20 of a user around a hair 21. Upon curing of the wax 18, the tweezer 12 is used to remove the wax 18 thereby removing the hair 21 from its follicle.

The portions 14, 16 of the tweezer 12 are integrally joined to form the tweezer 12. Each of the portions 14, 16 has a distal end 24. The distal ends 24 of the portions 14, 16 are designed for grasping onto a hair 21 for the purpose of removing the hair 21.

The upper portion 14 of the tweezer 12 has a wax cavity 26. The wax cavity 26 is integrally formed within the upper portion 14 such that the wax cavity 26 is designed for the holding and dispensing of the wax 18.

The upper portion 14 of the tweezer 12 has a wax plunger 28. The wax plunger 28 is slidably coupled to the upper portion 14 of the tweezer 12. The wax plunger 28 is in contact with the wax 18 in the wax cavity 26 of the upper portion 14 such that the wax plunger 28 is designed for biasing the wax 18 in the wax cavity 26 towards the distal end 24 of the upper portion 14.

The upper portion 14 of the tweezer 12 has a wax aperture 30. The wax aperture 30 is positioned on an end surface 32 of the distal end 24 of the upper portion 14. The wax aperture 30 is designed for allowing melted wax 18 to be dispensed from the upper portion 14 of the tweezer 12 when the wax 18 is biased towards the distal end 24 of the upper portion 14 by the wax plunger 28. This allows the user to utilize the wax 18 cured around a hair 21 in conjunction with the tweezer 12 to remove the hair 21 from its follicle.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A depilatory device for the removal of unwanted hair, the depilatory device comprising:

a tweezers for grasping onto a hair of a portion of a body of a user to facilitate removal therefrom, said tweezers comprising an upper portion and a lower portion;

a quantity of wax being dispensibly positioned in said upper portion of said tweezers such that a portion of said quantity of wax is dispensable onto skin of the user about the hair when said upper portion is heated to a temperature above a melting point of said wax; and wherein first ends of each of said portions of said tweezers are joined together to form said tweezers, free ends of each of said portions being movable toward and away from each other to permit grasping onto and removing the hair from its follicle upon curing of said wax;

wherein a cavity for storing said wax is formed in said upper portion, said cavity extending inwardly from said free end of said first portion and terminating near said first end of said upper portion;

a plunger member for selectively moving said wax outwardly of said cavity of said upper portion of said tweezers, said plunger member being slidably coupled to said upper portion such that said wax is selectively dispensable from said upper portion when said plunger member is moved towards said free end by the user.

2. The depilatory device as set forth in claim 1, wherein said cavity has an aperture for dispensing said wax therefrom, said aperture being positioned on an end tip surface of said free end of said upper portion and being fluidly coupled to said cavity such that said wax is dispensable through said aperture about the hair when said plunger member is moved towards said free end of said first portion.

3. A depilatory device for the removal of unwanted hair, the depilatory device comprising:

a tweezers for grasping onto a hair of a portion of a body of a user to facilitate removal therefrom, said tweezers comprising an upper portion and a lower portion;

a quantity of wax being dispensibly positioned in said upper portion of said tweezers such that a portion of said quantity of wax is dispensable onto skin of the user about the hair when said upper portion is heated to a temperature above a melting point of said wax; and wherein first ends of each of said portions of said tweezers are joined together to form said tweezers, free ends of each of said portions being movable toward and away from each other to permit grasping onto and removing the hair from its follicle upon curing of said wax;

wherein a cavity for storing said wax is formed in said upper portion, said cavity extending inwardly from said free end of said first portion and terminating near said first end of said upper portion;

a plunger member for selectively moving said wax outwardly of said cavity of said upper portion of said tweezers, said plunger member being slidably coupled to said upper portion such that said wax is selectively dispensable from said upper portion when said plunger member is moved towards said free end by the user;

wherein said cavity has an aperture for dispensing said wax therefrom, said aperture being positioned on an end tip surface of said free end of said upper portion and being fluidly coupled to said cavity such that said wax is dispensable through said aperture about the hair when said plunger member is moved towards said free end of said first portion.

* * * * *